United States Patent [19]
Godec et al.

[11] Patent Number: 5,310,683
[45] Date of Patent: May 10, 1994

[54] PROCESS FOR SIMULTANEOUS MEASUREMENT OF SULFUR AND NON-SULFUR CONTAINING COMPOUNDS

[75] Inventors: Richard Godec, Erie; Neil Johansen, Boulder; Donald H. Stedman, Englewood, all of Colo.

[73] Assignee: Sievers Research, Inc., Boulder, Colo.

[21] Appl. No.: 754,889

[22] Filed: Sep. 6, 1991

Related U.S. Application Data

[60] Division of Ser. No. 444,636, Dec. 1, 1989, abandoned, which is a continuation-in-part of Ser. No. 275,980, Nov. 25, 1988.

[51] Int. Cl.$^5$ ............................................. G01N 25/22
[52] U.S. Cl. .................................... 436/123; 422/98; 422/52; 436/156; 436/159
[58] Field of Search ................ 422/98, 52; 436/123, 436/156, 159

[56] References Cited
U.S. PATENT DOCUMENTS

| | | | |
|---|---|---|---|
| 4,352,779 | 10/1982 | Parks | 436/123 |
| 4,678,756 | 7/1987 | Parks | 436/123 |
| 4,843,016 | 6/1989 | Fine | 422/52 |

*Primary Examiner*—James C. Housel
*Assistant Examiner*—Lyle A. Alexander
*Attorney, Agent, or Firm*—Beaton & Swanson

[57] ABSTRACT

A process and apparatus for the simultaneous measurement of sulfur-containing compounds and organic compounds with or without sulfur in their structures. A detector cell allows simultaneous measurement of compounds that can be ionized in a flame and thereby cause the electrical conductivity of the flame to increase, and the selective measurement of sulfur-containing compounds which simultaneously form sulfur monoxide. Sulfur monoxide, upon mixing with ozone, emits light from 240 to 450 nm. The intensity of the light can be measured and related to the concentration of sulfur in the sample, while changes in electrical conductivity of the flame measured by imposing a voltage across the cell quantifies the organic compounds irrespective of whether or not they contain sulfur. Ratios of the signals of light intensity and electrical conductivity are different for each compound and, when the detector is coupled with a chromatographic separation column and process, this ratio facilitates the identification of unknown constituents in a mixture.

10 Claims, 6 Drawing Sheets

PROCESS FOR SIMULTANEOUS MEASUREMENT OF SULFUR AND NON-SULFUR CONTAINING COMPOUNDS

CROSS-REFERENCE TO RELATED APPLICATIONS

This is a divisional of copending application Ser. No. 07/444,636 filed on Dec. 1, 1989, now abandoned, which is a continuation-in-part of co-pending application Ser. No. 07/275,980 filed Nov. 25, 1988, for Process and Apparatus for the Detection of Sulfur.

FIELD OF THE INVENTION

This invention relates to a process and apparatus for simultaneously detecting and quantifying trace amounts of sulfur and non-sulfur containing compounds.

BACKGROUND OF THE INVENTION

Various processes have been devised for the measurement of the chemical components of a complex mixture separated by gas, liquid or supercritical fluid carriers, and for the measurement of the composition of gas, liquid and supercritical fluid streams or the gases evolved upon heating a solid matrix. Representative of such processes are detection by changes in physical properties of the streams, including changes in the refractive index and thermal conductivity. Another detection scheme is based on the measurement of electrical currents induced by the formation of ionic species during combustion of a stream (flame ionization). Irradiation of a stream using electromagnetic radiation and radioactive sources or changes in the absorption of electromagnetic radiation by components of a stream are also employed.

In general, these processes allow detectors that can be classified as either "general" or "universal" detectors. These detectors produce a response for all of the chemical constituents contained in a carrier stream (except for the eluent or carrier itself). Selective detectors, on the other hand, respond to specific chemical constituents based on one or more elements within each compound detected and/or unique physical or chemical properties of the components. Selective detection is often required when the chemical components of interest are present at low concentrations, together with much higher concentrations of other chemicals in the stream.

Detection systems can be further classified as being non-destructive detectors, in which the chemical composition of the stream is not altered by the measurement process, or destructive detectors, in which the sample is destroyed or chemically altered as a result of the measurement process. Generally, to use a destructive detector, such as a flame ionization detector, in combination with a selective detector, it is necessary to split the sample stream prior to measurement of the chemical constituents by the respective detectors. Difficulties in controlling the amount of the sample stream which flows into the different detectors using stream splitting has severely limited the utility of this technique.

In chromatographic analysis, the identity of a chemical compound is determined based on the "retention time" of the compound in a chromatographic system. The amount of the compound is determined based on the detector response. Typically, several analyses are performed using standard solutions of the test compound at different concentrations. Based on this information, a calibration curve is constructed by comparing the detector response (e.g. peak area) to the amount of injected compound. For both "universal" and "selective" detectors, retention time as well as response of a given chemical compound relative to a "standard" compound provide information regarding the identity of the chemical.

Once response factors for a wide range of chemical compounds are known, it is possible to determine the concentrations of different compounds based solely on their retention times and detection response without the need for constructing calibration curves for each individual component. For example, relative response factors using a flame ionization detector are available for a large number of hydrocarbons and other chemical compounds found in petroleum and petrochemical samples, thus greatly simplifying quantifications of these complex samples. Comparison of the relative response factors for compounds on two or more different detectors provides even more information regarding the identity of a particular chemical compound, since fundamentally different measurement techniques are employed.

An important class of selective detectors are devices for the selective measurement of sulfur-containing compounds. When present as impurities at low concentrations, sulfur-containing compounds are detrimental to a wide range of chemical processes. In consumer products, trace levels of sulfur-containing compounds can impart objectionable taste and odor to products. In petrochemical applications, trace sulfur contaminants can rapidly poison costly catalysts. For these reasons, numerous processes and apparatus have been developed for the measurement of low concentrations of sulfur-containing compounds in sample streams.

Representative of such processes is that disclosed in West German Patent No. 1,133,918 to H. Dragerwerk and B. Drager for the flame photometric detector (FPD). Sulfur-containing compounds are oxidized in a hydrogen/air flame to form diatomic sulfur $S_2$ in an electronically excited state. Emission of light from this species can be measured using a photomultiplier tube or similar light detection device equipped with an optical filter to eliminate the light emitted from other species in the flame. Through the use of different optical filters, the FPD can also be used for the measurement of phosphorus-containing compounds based on the emission of light from electronically excited phosphorus dioxide ($PO_2$) formed in the hydrogen/air flame. Compounds that do not contain sulfur or phosphorus cannot be measured using the FPD. However, compounds that do not contain sulfur or phosphorus can result in a decrease or "quenching" of the detector response for sulfur-and phosphorus-containing compounds. S. O. Farwell and C. J. Barinaga, Sulfur-Selective Detection with the FPD: Current Enigmas, Practical Usage, and Future Directions, 24 Journal of Chromatographic Science, 483 (1986).

The reactive sulfur and phosphorus species generated in the FPD flame are short-lived and therefore require that the light measurement device be located in close proximity to the flame. This basic design requirement has precluded the simultaneous operation of the FPD with other "universal" detection systems, such as the flame ionization detector. Of course, there is no such thing as a truly universal detector. For example, the flame ionization detector responds sensitively to nearly all organic compounds (excluding formaldehyde and formic acid) but not to inorganic compounds (e.g., $O_2$, $N_2$, Ar, $CO_2$, CO, $SO_2$, $H_2S$, COS, etc.).

Another example of selective detection of sulfur-containing compounds is that disclosed in U.S. Pat. Nos. 4,678,756 and 4,352,779 of R. E. Parks. According to this process, a sample is passed through a furnace containing a metal oxide catalyst to convert sulfur-containing compounds to sulfur dioxide. The sulfur dioxide is then passed through a second furnace, where the sample is mixed with hydrogen gas to facilitate the conversion of sulfur dioxide to hydrogen sulfide. The effluent of the second furnace is then directed into a reaction cell where the hydrogen sulfide is mixed with ozone and the resultant chemiluminescence is measured by means of a photomultiplier tube. In the system described by Parks, non-sulfur-containing compounds cannot be measured, since the expected products from the oxidation furnace (carbon dioxide and/or carbon monoxide) and from the reduction furnace (methane) either do not undergo an ozone-induced chemiluminescent reaction, or the light emitted from such reactions is eliminated through the use of optical filters.

Numerous other patents and publications may be found which disclose other approaches to the selective detection of sulfur-containing compounds. Gaffney and co-workers have described a technique for the measurement of reduced sulfur compounds (e.g., hydrogen sulfide, methanethiol, dimethyl sulfide, etc.) based on reactions of the sulfur-containing compounds with ozone to form electronically excited sulfur dioxide ($SO_2^*$) which then emits radiation in the 200 nm to 400 nm region of the spectrum. J. S. Gaffney, D. F. Spandau, T. J. Kelly, R. L. Tauner, Gas Chromatographic Detection of Reduced Sulfur Compounds Using Ozone Chemiluminescence, 347 Journal of Chromatography 121 (1985). This detection system does not permit measurement of all sulfur-containing compounds (e.g., sulfur dioxide) and suffers from interferences from non-sulfur-containing compounds such as olefins.

Birks and co-workers have described a sulfur selective detector based on fluorine-induced chemiluminescence. J. K. Nelson, R. H. Getty, J. W. Birks, Flourine Induced Chemiluminescence Detector for Reduced Sulfur Compounds, 55 Analytical Chemistry 1767 (1983). Reduced organic sulfur-containing compounds (e.g., mercaptans, sulfides, disulfides, etc.) react with molecular fluorine to form vibrationally excited hydrogen fluoride and other electronically and vibrationally excited species which emit radiation in the red and near infrared region of the spectrum. Inorganic sulfur-containing compounds (e.g., $H_2S$, $SO_2$, etc.) do not undergo fluorine-induced chemiluminescence, while many non-sulfur-containing compounds, such as olefins and aromatic hydrocarbons, do react and interfere in the measurement of sulfur compounds.

Other workers have described a detection system based on the reaction of sulfur-containing compounds with chlorine dioxide. These reactions result in the formation of electronically excited diatomic sulfur, which emits radiation in the visible region of the spectrum (250 to 450 nm).

None of these previously reported systems for the measurement of sulfur-containing compounds permit the simultaneous measurement of non-sulfur-containing compounds, without the need for splitting the sample to a second "universal" detector system.

Halstead and Thrush have described the chemiluminescent reaction of sulfur monoxide with ozone. The Kinetics of Elementary Reactions Involving the Oxides of Sulphur III. The Chemiluminescent Reaction Between Sulphur Monoxide and Ozone, C. J. Halstead, B. A. Thrush, 295 Proceedings of the Royal Society, London, 380 (1966). Sulfur monoxide, produced from sulfur dioxide using a microwave discharge, was reacted with ozone. One of the reaction products was identified as electronically excited sulfur dioxide. The emission spectrum from this species was recorded and found to extend from 280 to 420 nm, with maximum emission at 350 nm.

Previous studies have shown that sulfur monoxide is one of the species formed in the combustion of sulfur compounds in a flame. Sulfur Chemistry in Flames, C. H. Muller, et al., in 17th International Combustion Symposium, pp 867–879 (1989) and Experimental and Numerical Studies of Sulfur Chemistry in $H_2/O_2/SO_2$ Flames, M. R. Zachariah, O. I. Smith 69, Combustion and Flame 125 (1987). Under the typical operating conditions of the FPD, sulfur monoxide is present at about 10 times the level of diatomic sulfur.

On the basis of these observations, Benner and Stedman reported the development of a "Universal Sulfur Detector" (USD) based on the formation of sulfur monoxide in a hydrogen/air flame and subsequent detection of SO based on a chemiluminescent reaction with ozone. R. L. Benner, D. H. Stedman, Universal Sulfer Detection by Chemiluminescence, 60 Analytical Chemistry 1268 (1989). The original embodiment of the USD was a continuous monitor for the measurement of the total concentration of sulfur-containing compounds in ambient air. The USD is also described in the parent U.S. patent application Ser. No. 07/275,980. In this design, the air stream containing the sulfur compounds is mixed with an excess of hydrogen in a quartz burner assembly equipped with an external ignition source. A quartz sampling probe is used to collect sulfur monoxide and other products from the flame for transfer to a modified nitric oxide/ozone chemiluminescence detector.

This detection system was found to provide greater sensitivity for the measurement of sulfur-containing compounds than existing sulfur-selective detectors and did not suffer interferences in the measurement of sulfur species due to the presence of higher concentrations of non-sulfur species such as water, carbon dioxide and heptene.

The USD is designed so that the sulfur-containing compounds are contained in an air stream which is required to support combustion when mixed with a second stream containing hydrogen gas. The optimum gas flow rates were determined to be 400 to 500 mL/min of air and 300 mL/min of hydrogen. The optimum internal diameter for the quartz sampling probe was reported as about 0.1 mm. A key feature of the system reported by Benner and Stedman was the need to add a halogenated compound, such as $CF_2Cl_2$, into the air stream in order to achieve stable instrument baseline and long term instrument stability. The fundamental design of the USD precludes the measurement of non-sulfur containing compounds by conventional means such as the detection of ionic species produced in the flame.

SUMMARY OF INVENTION

The present invention describes a process and apparatus for the simultaneous measurement of sulfur-containing compounds and non-sulfur-containing compounds based on the combustion of species in the hydrogen/air flame of a flame ionization detector, measurement of the ionic species produced in the flame, and concurrent withdrawal of sulfur monoxide produced in the flame and measurement of the sulfur monoxide by ozone-induced chemiluminescence.

The integrated detection system simultaneously measures organic compounds capable of producing ionic species upon combustion in the hydrogen/air flame and selectively measures all sulfur-containing compounds based on conversion of these sulfur-containing compounds in the same hydrogen/air flame to form sulfur monoxide, which is withdrawn from the flame and detected by means of ozone-induced chemiluminescence.

An important advantage of the present integrated detector device is that it is not necessary to split the sample stream before it enters the detector cell. The selective detection system simultaneously forms both sulfur monoxide, from which sulfur-containing species are measured, and ions containing carbon, from which organic compound concentrations can be deduced. This device provides a means for direct operation of a "universal" detector (such as the flame ionization detector) and selective detection, without the need for splitting the sample stream.

In addition, in the present invention the response of two different detectors for the same compound is simultaneously measured, which greatly simplifies use of relative response factors in the identification of chemical compounds.

DETAILED DESCRIPTION OF THE PREFERRED EMBODIMENT

Figure 1:
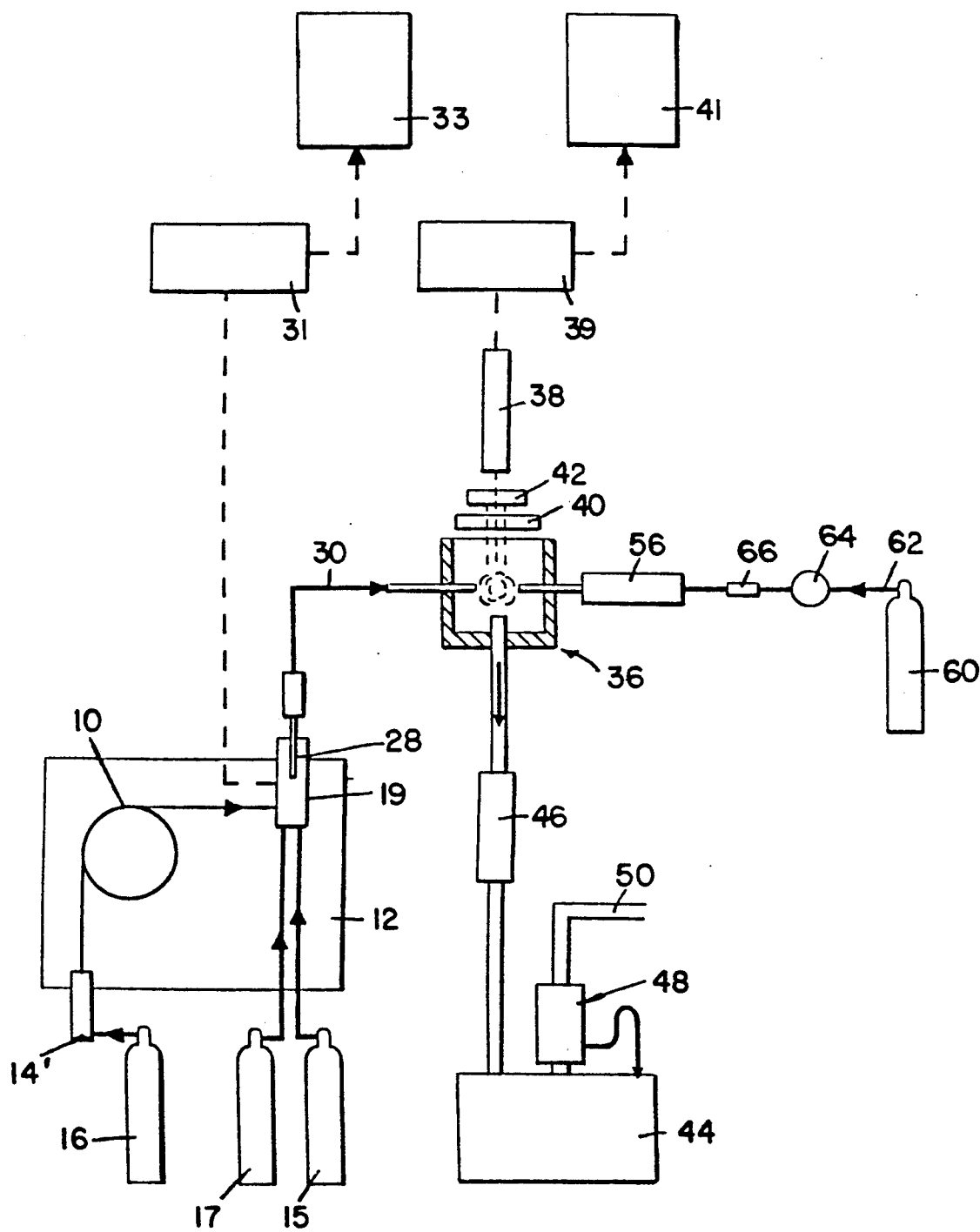
FIG. 1 is a schematic diagram of a preferred embodiment of the detector apparatus constructed in accordance with the present invention.
Figure 2:
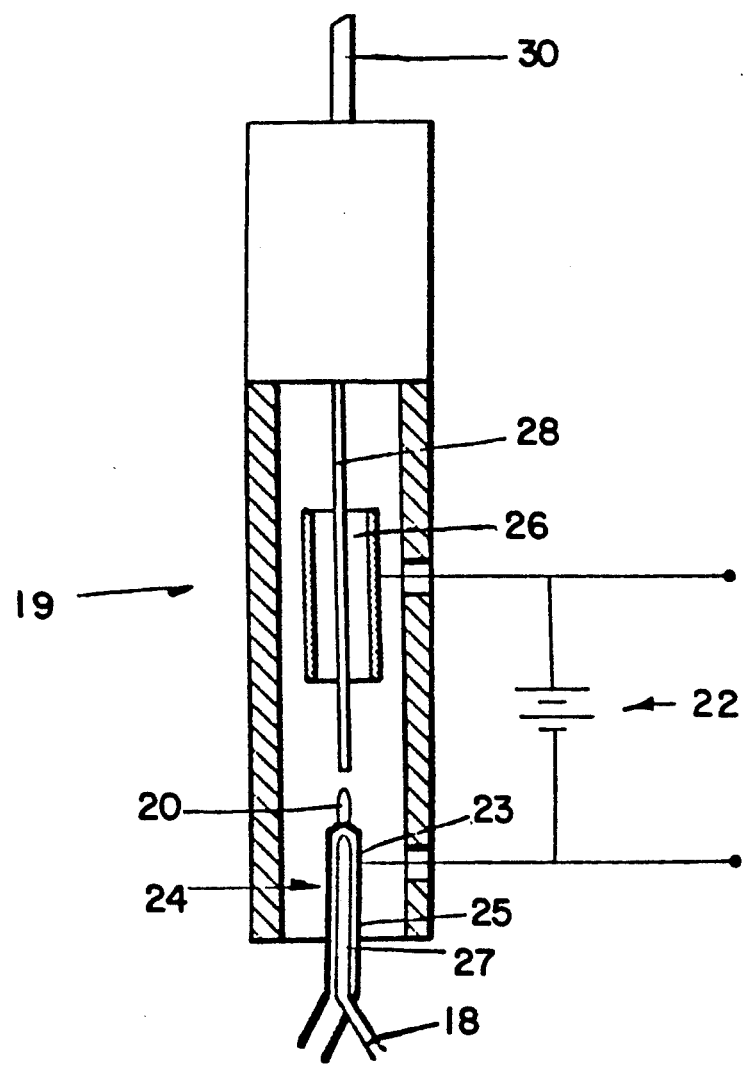
FIG. 2 is a detailed view of the flame source and flame sampling probe.

There is shown in FIG. 1 a preferred embodiment of the apparatus for the simultaneous detection of sulfur-containing compounds and non-sulfur-containing compounds after elution from a chromatographic column. The column 10 is contained in an oven 12, has an injection port 14 for injection of the sample and a supply 16 of the chromatographic mobile phase consisting of either a gas, liquid or supercritical fluid source. The effluent of the chromatographic column 10 is directed into the inlet 18 of an apparatus 19 for the combustion of the chemical constituents of the carrier stream in a hydrogen/air flame 20. A commonly available flame ionization detector may be used, if adapted as described below. A hydrogen gas source 17 and a compressed air or oxygen source 15 is in fluid communication with the interior of combustion apparatus 19. Standard means for adjusting the flow of these gases to create an appropriate flame may also be included and are well known in the art. As seen in FIG. 2, an external electrical potential 22 is applied between the base of the flame 20 and a metal tube 26, which serves as a collector for ionic species formed in the flame. The existence and quantity of ionic species formed in the flame 20, are derived from the current generated between the base of the flame and the metal tube 26. The current data is transferred to a microprocessor unit 31, which is capable of displaying the current detected as a function of time on a recorder 33.

In conjunction with the measurement of ionic species formed in the flame, a flame sampling probe 28 is positioned above the flame to withdraw 90-95% of the flame gases from the flame assembly via a transfer line 30 into a chemical reaction cell 36. In the chemical reaction cell 36, the flame gases are mixed with a stream containing ozone produced by means of an electrical discharge of air or oxygen. Sulfur monoxide and other reactive species formed in the flame 20 will be carried to the chemical reaction cell 36 via the transfer line 30, and will undergo chemical reactions with ozone to produce species such as sulfur dioxide in an excited electronic state, which will emit radiation.

The radiation emitted by the transient excited species is measured by means of a photomultiplier tube 38 after passage through a quartz window 40 and an optical filter 42. A vacuum pump 44 is used to withdraw the gases from the flame via the sampling probe 28, the transfer line 30 into the chemical reaction cell 36, and withdraw the gaseous products after completion of the chemiluminescent reaction from the reaction cell 36. A chemical trap 46 is used prior to the vacuum pump 44 to remove reactive chemical compounds, such as ozone and oxides of nitrogen, to prevent degradation of the vacuum pump and pump oil. A gas ballast and an oil return filter 48 is connected to the exhaust of the vacuum pump to facilitate the removal of water vapor and other gases from the vacuum pump 44 and the recycling of oil vapor from the pump exhaust. The pump 44 is exhausted out vent 50.

A detailed view of an embodiment of the flame source and flame sampling probe 28 is shown in FIG. 2. The flame sampling probe 28 consists of a high purity (>99.99%) aluminum oxide tube with an internal diameter of 0.020 in. and a length of 3.2 to 4.2 in., with minimal contamination of the probe material by silicon dioxide. In a preferred embodiment, the probe material may be either a high purity ceramic or high purity crystalline sapphire or ruby tube.

In the ionic detector apparatus 19, the sample stream to be analyzed is mixed with hydrogen gas and enters the flame jet 24. The flame source is comprised of a flame jet 24 that extends into the body of the ionic detector 19. The flame jet 24 is comprised of an outer chamber 25 and an inner tube chamber 27. The outer chamber 25 is in fluid communication with the source of hydrogen gas 17, and the inner tube chamber is in fluid communication with column 10 via inlet 18. The base of the ionic detector 19 is in fluid communication with the source of compressed air or oxygen 15. A stream of air is passed around the exterior of the tube and mixed with the stream containing the hydrogen and sample at the outlet of the tube 23.

An external ignition source is used to initiate combustion of these gas streams. In the preferred embodiment, the flow rate of the sample stream is 0.5 to 30 mL/min, the flow rate of the hydrogen gas stream is 170 to 190 mL/min and the flow rate of the air or oxygen stream is 275 to 350 mL/min.

The high purity aluminum oxide sampling probe 28 is positioned 4 to 8 mm from the top of the flame jet 24, and the height can be adjusted by means of a positional set-screw (not shown).

Exhaust gases from the flame 20 are withdrawn by means of a vacuum pump 44 through a transfer line 30 which is constructed of a chemically inert material to facilitate complete transfer of sulfur monoxide and other flame exhaust gases into the chemiluminescent reaction chamber 36.

In the preferred embodiment, the transfer line 30 is comprised of a 5 ft. length of 1.7 mm ID by ⅛ in. OD tubing composed of PFA, which has been treated with carbon black or other opaque materials in order to prohibit the passage of light through the walls of the transfer line tubing and into the chemiluminescent cell.

The present invention is distinctly different from the USD system of Benner and Stedman discussed above. As previously noted, the design of the USD precluded the measurement of non-sulfur-containing compounds based on the formation of ionic species in the flame. In contrast with USD, in the present invention the sample is mixed with a hydrogen stream and then is mixed with air and the temperature of the hydrogen/air flame 20 is much higher ($>150°$ C.) due to the higher gas flow rate employed and the use of a smaller size flame than the diffuse flame employed in the USD. The higher flame temperatures are important in the formation of ionic species from organic compounds during combustion. The optimum materials to be used for sampling the flame exhaust gases in the of the present invention are high purity aluminum oxides, with minimal contamination by silicon dioxide, in contrast to the pure silicon dioxide (quartz) sampling probe employed in the USD. Use of a sampling probe 28 composed of silicon dioxide (quartz) in the present invention resulted in lower overall sensitivity of the detector for sulfur-containing compounds versus a high purity aluminum oxide sampling probe. Finally, the present invention does not require the addition of a halogen-containing compound to the air stream for baseline stability.

Figure 3A:
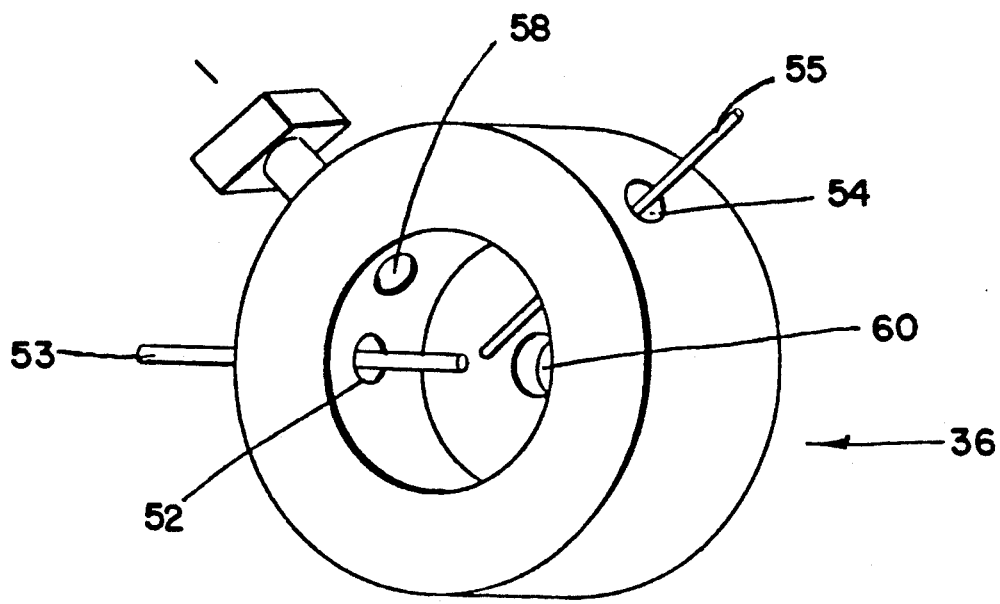
FIG. 3(A-B) shows a front and back elevational view of the preferred embodiment of the chemiluminescent reaction cell.
Figure 3B:
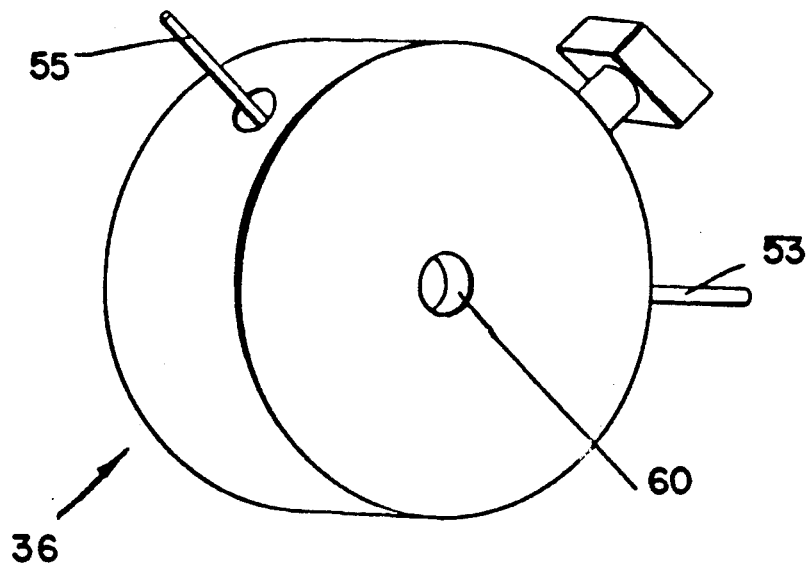

Detailed views of the chemiluminescent reaction cell 36 are shown in FIG. 3. The cell 36 is composed of aluminum and machined to an internal volume of about 10 cubic centimeters. There are four ports in the reaction cell 36. Port A 52 is the sulfur monoxide inlet, port B 54 is the ozone inlet from the ozone generator, port C 58 is the pressure transducer used to monitor the internal cell pressure and port D 60 is the vacuum outlet. A sulfur monoxide inlet tube 53, in fluid communication with transfer line 30, enters through Port A 52 and into the interior of reaction cell 36. An ozone inlet tube 55 enters through Port B 54 and into the interior of reaction cell 36. In a preferred embodiment, the ends of sulfur monoxide inlet tube 53 and the ozone inlet tube 55 are within 5 millimeters.

Ozone inlet tube 55 is in fluid communication with ozone generator 56. A source of compressed air or gas 60 is fed through conduit 62, via regulator 64 and filter 66, into ozone generator 56. Ozone generator 56 consists of an electrical discharge device that produces consistent and quantifiable amounts of ozone.

On the face of the chemical reaction cell 36 opposite the vacuum outlet 60, the quartz window 40 is held in a sealing relationship. All gases exit the reaction cell 36 via vacuum Port D 60. Light emitted by transient excited species within the interior of the reaction cell 36 passes through the quartz window 40, through the optical filter 42, and is measured at the photomultiplier tube 38. Data concerning the quantity of light generated is transferred to controller 39 for display on recorder 41.

EXAMPLE 1

In this Example, the apparatus shown in FIGS. 1, 2 and 3 consists, in part, of a Hewlett Packard Model 5890 gas chromatograph equipped with a 30 m × 0.32 mm ID fused silica capillary column 10, coated with a 4 micrometer film of methyl silicone (Supelco, Inc.). A helium carrier gas operated at a flow rate of about 2 mL/min is used to transfer organic compounds and sulfur-containing compounds from a heated injection port 14, through the chromatographic column 10 and into the integrated organic/sulfur detection system. The flame sampling probe 28 consists of a 3.2 cm × 0.5 mm ID ceramic probe positioned 6 mm from the tip of the flame jet 24. The instrument for the measurement of ozone-induced chemiluminescence of the flame exhaust gases is a Sievers Research, Inc. Model 350 Sulfur Chemiluminescence Detector equipped with an Edwards Model E2M-1 vacuum pump.

Figures 4A, 4B:
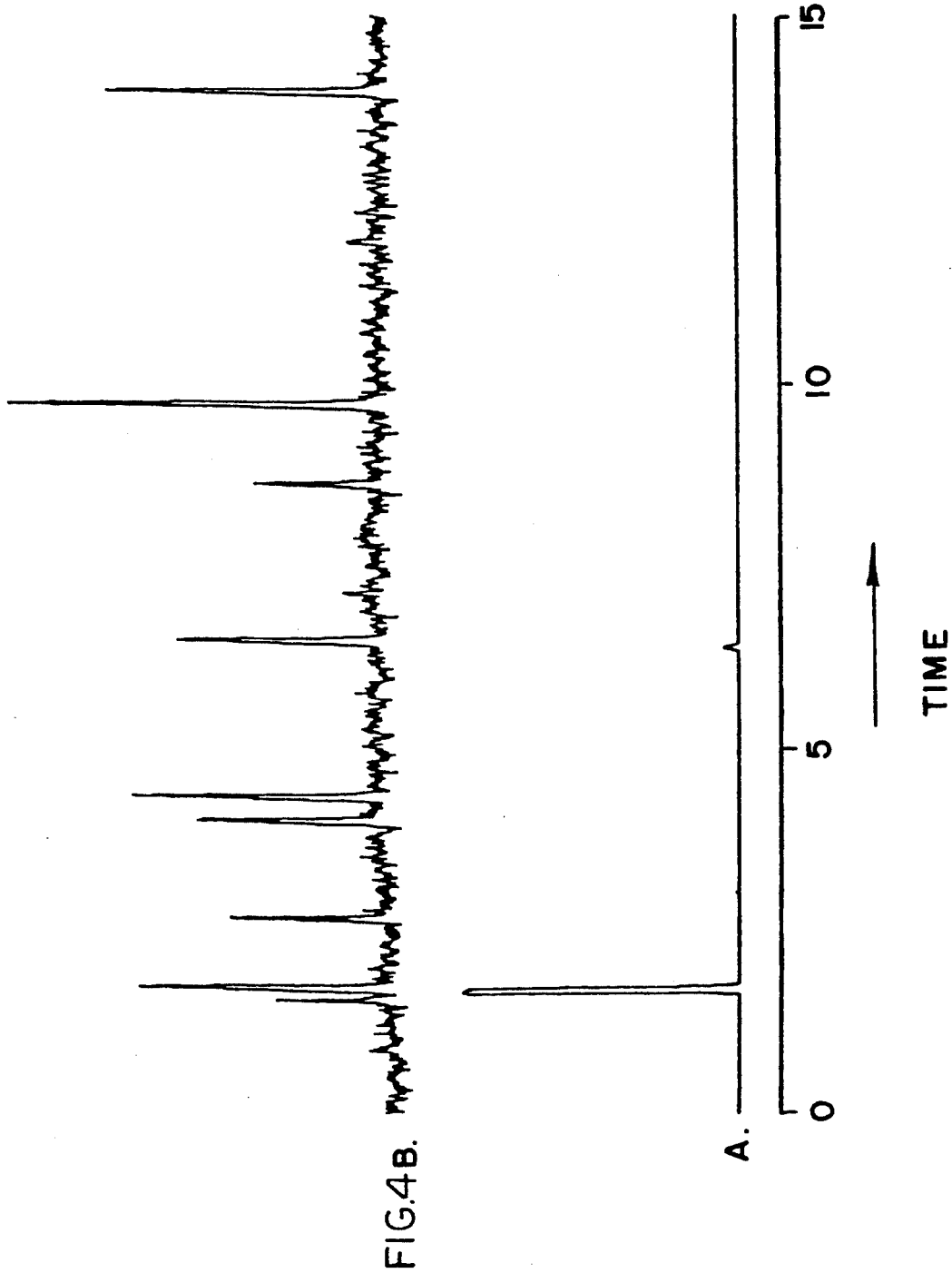
FIGS. 4(A-B) and 5(A-B) are illustrative representation of chromatograms produced by the detectors in accordance with the present invention and gas chromatography.

As shown in FIG. 4, when a mixture containing parts-per-million levels of nine different sulfur-containing compounds in gaseous propylene is injected into this system, two different detector signals are obtained, simultaneously, from a single sample injection. The lower chromatogram A is obtained by the measurement of ionic species produced in the hydrogen/air flame from the combustion of organic compounds. The upper chromatogram B is obtained by collection of sulfur monoxide formed in the flame and measurement of the radiation emitted from the flame exhaust gases after they are mixed with ozone.

In chromatogram A, the sulfur-containing compounds are present at much lower concentrations are not detected. Only propylene and two other non-sulfur-containing compounds, ethanol and hexane which are present in the sample, are under these operating conditions. In contrast, only the sulfur-containing compounds are detected by the second component of the integrated detection system (chromatogram B), even though the non-sulfur-containing compounds are present at more than a million times greater concentrations. In addition, this example illustrates another key feature of the present invention. Under the conditions employed, carbonyl sulfide and propylene are not chromatographically resolved, with both compounds exiting the chromatographic column and entering the detection system simultaneously. In contrast with other sulfur-selective detection systems, the presence of a much higher level of a non-sulfur-containing compound (propylene) does not reduce or in any way interfere with the measurement of the much lower level of carbonyl sulfide in the sample.

EXAMPLE 2

Figure 5A:
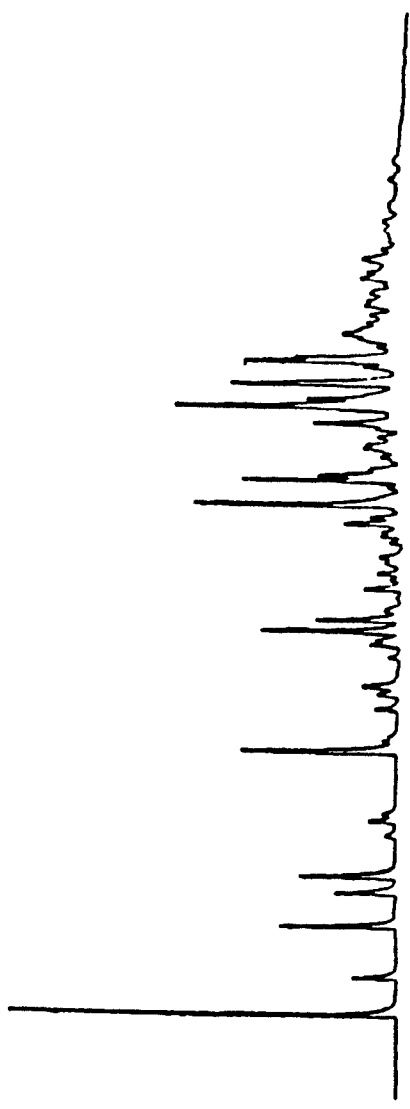
Figure 5B:
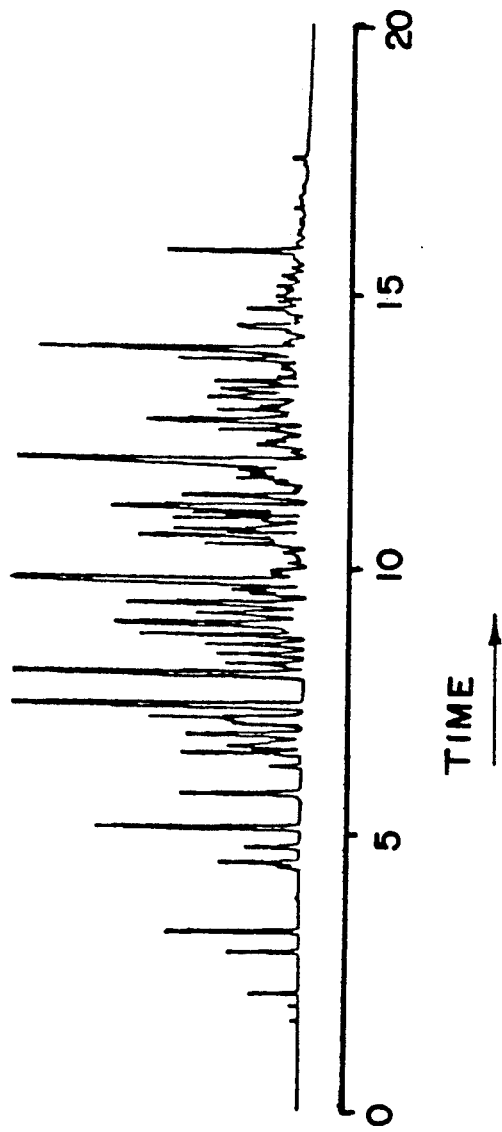

Utilizing the same apparatus as previously described in Example 1, but with a 30 m × 0.32 mm ID fused silica capillary with a 2 micrometer coating of methyl silicon, and under similar conditions as detailed in Example 1, a sample of a naphtha feed stock was injected into the gas chromatograph and the organic components and the sulfur-containing compounds measured using the integrated detection system. As illustrated in FIG. 5, the lower chromatogram C demonstrates that the naphtha sample is primarily composed of a large number of aliphatic, aromatic and olefinic hydrocarbons. The upper chromatogram D shows the input from the chemiluminescent detector portion of the detection system. The complex nature of this sample does not permit complete resolution of all of the components and, in particular, trace levels of the sulfur-containing compounds and higher levels of the non-sulfur-containing hydrocarbon compounds cannot be measured with other detection systems. In the present invention, the trace levels of the sulfur-containing compounds can be sensitively measured by the ozone-induced chemiluminescence component, while the higher levels of hydrocarbons are simultaneously measured by the flame ionization component of the detection system.

EXAMPLE 3

The apparatus detailed in Example 1 was modified by removal of the flame sampling probe 28 from the system and adjustment of the hydrogen flow rate to about 30 mL/min and the air flow rate to about 250 mL/min. These flame conditions are the same as those employed in the standard operation of a flame ionization detector. Under these modified conditions, a sample containing a mixture of hydrocarbons was injected into the chromatographic system and the flame ionization response for each compound was measured relative to normal hexane. The flame sampling probe 28 was then reinstalled, flow rate adjusted to the conditions detailed in Example 1 and the sample re-injected. The response relative to hexane (Relative Response Factor, or RRF) for representative hydrocarbons determined under these two different operating conditions are shown in Table 1. These data show that the operating conditions of the integrated detector system do not significantly change the RRF compared with those obtained using standard FID operating conditions. This is remarkable considering the large differences in the gas flow rates between standard FID and the conditions employed in the present invention. This means that it will be possible to directly apply the extensive compilation of relative response factors published for a standard FID to data obtained with the new simultaneous detection system.

Also shown in Table 1 are the response factors for selected sulfur compounds relative to diethylsulfide. Response factors are calculated relative to diethylsulfide since hexane produces no response in the sulfur-selective portion of the simultaneous detection system. As can be seen from this data, significant differences exist in the relative responses of different sulfur compounds when measured by the different detectors of the simultaneous detection system, which in principle, can be used as a means of compound identification.

TABLE 1

| COMPOUND | RRF SULFUR MODE FID | RRF STANDARD FID | RRF SULFUR DETECTOR |
| --- | --- | --- | --- |
| c-2-hexane | 0.19 | 0.19 | 0 |
| Benzene | 1.72 | 1.72 | 0 |
| Toluene | 2.85 | 3.15 | 0 |
| n-octane | 3.41 | 3.69 | 0 |
| o-xylene | 1.28 | 1.45 | 0 |
| Napthalene | 0.32 | 0.39 | 0 |
| Dimethyldisulfide | 0.63 | | 2.09 |
| Diethyldisulfide | 0.86 | | 1.67 |

EXAMPLE 4

The apparatus detailed in Example 1 was modified for use as a supercritical fluid chromatograph. A CCS model 7000 SFC fluid controller was used to deliver supercritical carbon dioxide. A 150 mm × 1 mm stainless steel column packed with 3 micrometer particles of octadecyl silyl treated silica was housed in an HP 5890 oven for temperature control. A short length (about 5 cm) of 0.025 m ID fused silica tubing was connected between the exit of the column and the inlet of the flame source to act as a restrictor. Combustion gases from the hydrogen air flame were collected using a 3.2 cm × 0.020 in. ID sapphire tube 28.

Figure 6B:
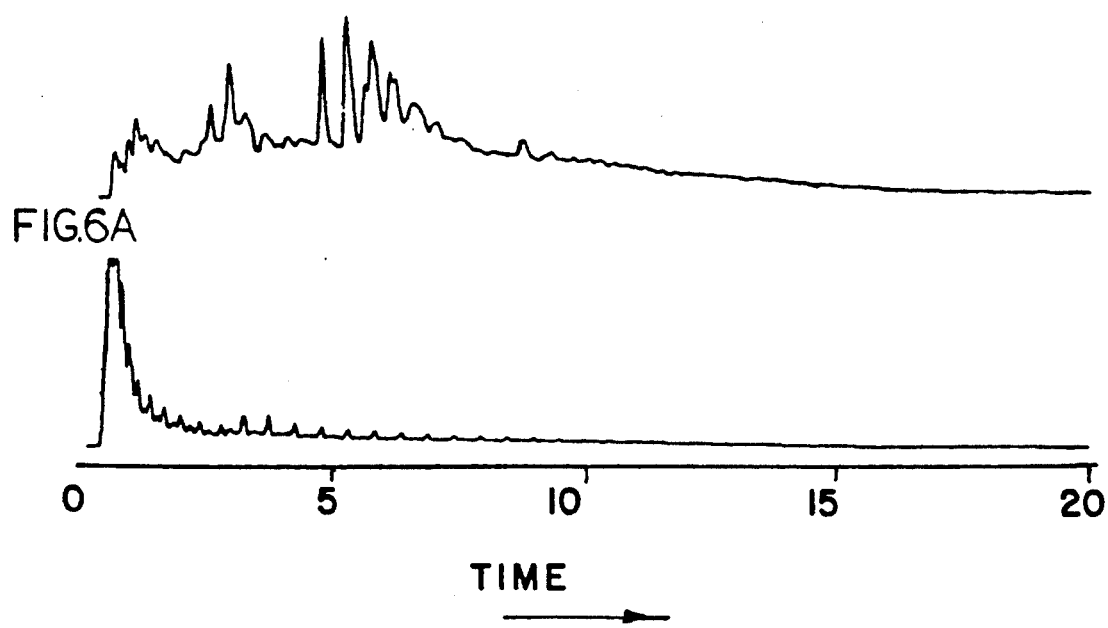
FIG. 6(A-B) illustrates representations of chromatograms produced by the detectors in accordance with the present invention and supercritical fluid chromatography.

FIG. 6 shows the simultaneous analysis of organic compounds (chromatogram E) and sulfur-containing compounds (chromatogram F) present in a sample of crude oil using the present invention coupled with supercritical fluid chromatography. Previous attempts to employ existing sulfur-selective detectors for supercritical fluid chromatography, even without simultaneous measurement of non-sulfur-containing organic compounds, have not been successful due to low sensitivity and large changes in the detector baseline during pressure programming. In the present invention, no increase in the baseline is observed during pressure programming for either the non-sulfur-containing flame ionization detector response E or the sulfur-selective chemiluminescence detector response F.

The description and examples above are given as a means of illustrating the present invention. They are not, however, intended to limit or narrow the invention as set forth in the claims below.

We claim:

1. A process for the simultaneous detection of sulfur-containing compounds using chemiluminescence and non-sulfur-containing compounds using flame ionization, comprising:
    combusting a fluid stream containing a mixture of sulfur-containing compounds and non-sulfur-containing compounds in a flame to produce sulfur monoxide, ionic species, and other products;
    detecting said ionic species by subjecting said flame to an applied electrical potential and measuring the conductance of said flame during said step of said combusting the fluid stream; and
    collecting said sulfur monoxide from the flame;
    reacting said sulfur monoxide to form a chemiluminescent species;
    detecting the chemiluminescent species which is representative of the sulfur compounds in the fluid stream.

2. A process as described in claim 1 wherein said sulfur monoxide is detected by reacting said sulfur monoxide to form an excited-state species and measuring the light emitted from said species.

3. A process as described in claim 2 wherein said species is formed by contacting said sulfur monoxide with ozone.

4. The process as described in claim 1 wherein said fluid stream is mixed with hydrogen and then air is added to the fluid stream mixed with hydrogen to generate said flame.

5. The process as described in claim 4 wherein the flow rate of said fluid stream is between about 0.5 to 300mL/min., the flow rate of the hydrogen is between about 170 to 190 mL/min., and the flow rate of the air is between about 275 to 350 mL/min.

6. A process as described in claim 1 wherein said sulfur monoxide is collected from the flame by means of a sampling probe and at least about 90% of the gases produced in said flame enter said sampling probe.

7. A process as described in claim 6 wherein said sampling probe is made of material that is inert under the operating conditions utilized.

8. The process as described in claim 7 wherein said sampling tube is comprised of a high purity aluminum oxide tube, containing substantially no silicon dioxide.

9. A process for the simultaneous detection of sulfur-containing compounds using chemiluminescence and non-sulfur-containing compounds using flame ionization in a fluid stream comprising:

mixing said fluid stream with a stream of hydrogen gas to form a stream of fluid and hydrogen;

mixing said stream of fluid and hydrogen with a stream of air or oxygen to form a stream of fluid, hydrogen and air or oxygen;

combusting said stream of fluid, hydrogen and air or oxygen in a flame to produce sulfur monoxide, ionic species and other products;

applying an electrical potential to said flame during said step of combusting said stream of fluid, hydrogen and air or oxygen;

measuring the conductance of said flame during said step of combusting said stream of fluid, hydrogen and air or oxygen;

collecting said sulfur monoxide from the flame by means of a sampling probe;

reacting said sulfur monoxide to form an excited-state species; and measuring the amount of light emitted from said species.

10. The method of claim 9, wherein the electrical potential is applied through an electrical conductor positioned above the flame to produce a current flow between the flame and the electrical conductor.

* * * * *